United States Patent [19]

Wolk et al.

[11] 4,264,302

[45] Apr. 28, 1981

[54] ORTHODONTIC APPLIANCE

[76] Inventors: Roger Wolk, 28 Malibu Colony Dr., Malibu, Calif. 90265; Ivan Bekey, 4624 Charter Charge Dr., Annandale, Va. 22003

[21] Appl. No.: 18,643

[22] Filed: Mar. 8, 1979

[51] Int. Cl.³ .............................................. A61C 3/00
[52] U.S. Cl. ..................................... 433/5; 242/107.6
[58] Field of Search ................... 32/14 D, 14 E, 14 A; 242/107.5, 107.6; 433/5

[56] References Cited

U.S. PATENT DOCUMENTS

| | | | |
|---|---|---|---|
| 2,474,899 | 7/1949 | Hutt | 242/107.6 |
| 2,968,097 | 1/1961 | DeWoskin | 32/14 D |
| 3,012,736 | 12/1961 | Brust | 242/107.5 |
| 3,654,702 | 4/1972 | Kelly, Jr. | 32/14 A |
| 3,686,757 | 8/1972 | McVickers et al. | 32/14 D |
| 3,918,159 | 11/1975 | Andrews | 32/14 D |
| 3,921,295 | 11/1975 | James | 32/14 E |
| 4,074,433 | 2/1978 | Nelson | 32/14 E |
| 4,115,921 | 9/1978 | Armstrong | 32/14 D |

*Primary Examiner*—Gene Mancene
*Assistant Examiner*—John J. Wilson
*Attorney, Agent, or Firm*—Philip D. Junkins

[57] ABSTRACT

An extraoral orthodontic appliance including a harness for mounting on the head and/or neck of a patient and connected to a conventional corrective tractive apparatus, such as a set of J-hooks, a face bow or a chin cup, by traction force devices (force modules) mounted on each side of the harness. The force modules incorporate force reels that are internally force-biased by inexpensive non-constant (cumulative) force, clock-type springs of large extension which can be adjusted to desired tractive force levels by winding and preset so as to apply a substantially constant tractive force during treatment periods, regardless of movement of the patient's head or jaw. Further, the force modules may include means to limit the extent to which the corrective tractive apparatus can be extended and retracted thereby protecting the patient from injury during placement and removal of the appliance or accidental uncontrolled retraction.

11 Claims, 14 Drawing Figures

ORTHODONTIC APPLIANCE

BACKGROUND OF THE INVENTION

Orthodontics is the specialty branch of dentistry dealing with the treatment of malpositioned teeth and the correction of improper relationships between the upper and lower dental arches. Generally, the practice of orthodontic treatment is effected by the application of mechanical forces to selected teeth or to an entire dental arch when malocclusion involving a full arch needs to be corrected. Numerous intraoral appliances are available for mounting directly on the patient's teeth with resilient wires or elastic bands used to provide corrective forces for moving malpositioned teeth into correct alignment.

An orthodontic headgear is an extraoral harness which includes a strap or arrangement of several straps configured to fit around the back of a patient's neck and/or around a patient's neck and over the patient's head and which is releasably connectable to a corrective extraoral tractive apparatus (face bow, set of J-hooks, chin cup, or the like) which is designed to apply a traction or posterior force to the patient's dental arch or teeth. Headgears have typically employed elastic bands or straps made of rubber, surgical latex or similar acting elastomers (in loop or multiple loop configuration) which are elongated and coupled to the teeth (usually through a wire face bow) to deliver the desired traction forces.

The term headgear as used in this application refers to a strap (or band) or series of straps (or bands) configured for either cervical mounting (single strap or band extending around the neck) or occipital (or calvarial) mounting (multiple straps or bands, one providing cervical anchorage and one or more providing occipital anchorage).

Commonly utilized types of orthodontic headgears present problems during orthodontic treatment. Principal difficulties arise with regard to the rubber, latex or elastomer bands normally used to provide traction forces. Such bands are manufactured with a guaranteed force predictability within the range of about ±15-25% of rated pull force at a given elongation. Thus, a new latex type force band or loop rated at 8 ounces pull at an elongation of 3 times its slack diameter might, in fact, provide as little as 6 or as high as 10 ounces of pull force at such elongation. Further, such bands have a short life and are elastically unstable, and the restoring force delivered by an elastic band for a given elongation (initial pull rating) drops off quite rapidly with time with the result that the patient must be instructed to replace the bands at frequent and regular intervals. More importantly, with common types of headgears utilizing such bands, as the patient moves his or her head, the elongation of the bands changes with the result that the force actually applied or delivered by the appliance may vary by a factor of ±2 to 3 times the desired force level due to the rapid degree of force change (increase or decrease with elongation or relaxation) from the rated force at the point of elongation establishing such force.

An important factor in an effective orthodontic treatment program is the ability to apply a known, substantially constant corrective force in the direction desired. With conventional headgears employing elastic force bands this ability is difficult to achieve because the treatment program, to a great degree, relies on full patient cooperation with respect to timely replacement of the bands. Even if the patient is fully cooperative, the variation of actual pull force between bands of the same rating and the rapid decrease in restoring force of such bands with time negates the probability of delivery of the desired substantially constant corrective force. This can increase the time required to accomplish a correction, or limit the effectiveness of the correction.

More recently, orthodontic headgears have been proposed, designed and provided with various types of metalic springs to apply corrective forces to a patient's teeth or jaws. In U.S. Pat. No. 3,526,035 granted to M. M. Armstrong there is disclosed a headgear using two wire coil springs to apply corrective bilateral forces to a patient's teeth or jaws. Such springs provide restoring forces (depending on their elongation) which are very stable and predictable over long periods of use, but the restoring forces are rapidly cumulative (rapid increase with spring elongation) so that for changes in spring elongation non-constant restoring forces are developed. Further, when the springs are utilized in a manner in which the nominal force is generated by an extension which is a large fraction of the spring resting length, small changes in its length cause large changes in applied force loads. Thus, during use of the orthodontic headgear as disclosed by Armstrong, movement of the patient's head (up, down or sidewise) and movement of the mandibular arch with respect to the maxillary arch results in large percentage extensions and retractions of the respective coil springs with the result that the spring-generated tractive forces vary significantly from the desired (pre-set) corrective force level.

U.S. Pat. No. 3,686,757, granted to J. C. McVickers and E. A. Leatherman, discloses an orthodontic appliance including a harness carrying force-applying members adapted to apply constant predetermined forces to a face bow or chin cup. Each force-applying member includes a flat, non-cumulative force, type of spring which provides a constant pull force as it is extended (or unwound) and as it rewinds. While the force-applying springs of the McVickers et al patent constant forces to the corrective appliance at all times, including when the head of the wearer is moved either from side to side or up and down, the constant force of each force member is predetermined by the characteristics of the spring contained therein. Thus, their force level cannot be changed or adjusted except by substitution of a spring having characteristics providing the different desired level of constant force. Non-cumulative force springs are expensive, require special heat treating and means for backwinding or otherwise pre-stressing the spring, occupy greater volume than cumulative (non-constant) force springs, and require careful attention during design and manufacture to the material from which they are made, to the thickness and width dimensions of the flat spring material, and to edge treatment in order to attain reasonable performance and life.

The orthodontic appliance of this invention overcomes the problems of: large variability of applied corrective force from the desired (pre-set) force level for wire coil springs used in the Armstrong type headgears during normal movements of the patient's head and/or jaws; and non-adjustability of the force level of costly non-cumulative force springs of the type used in the McVickers et al headgears. Rather, relatively inexpensive clock-type springs which develop non-constant (cumulative) forces (during their winding and unwinding) are used extraorally in a manner that results in the application of a substantially constant pre-determined corrective force during the orthodontic treatment program. Even though with head or jaw movement the clock-type springs of the appliance unwind and/or wind, the resultant changes in force developed are small compared to the preset or desired force level due to the movements entailing only a small portion of the total available extension of the spring. Further, the clock-type springs of the appliance can be wound or unwound by the treating orthodontist to adjust the magnitude of the applied corrective force level thereby eliminating the need for changing springs to obtain desired variations in force levels during a treatment program or between patients.

SUMMARY OF THE INVENTION

The present invention is an extraoral orthodontic appliance including a harness for mounting on the head and/or neck of a patient and connected to a conventional corrective tractive apparatus, such as J-hooks, a face bow or a chin cup by traction force devices mounted on each side of the harness. The traction force devices apply a substantially constant predetermined force to the corrective tractive apparatus at all times during which the patient wears the orthodontic appliance including when the head of the patient is moved either up and down or from side to side and as movement of the dental-facial structure occurs. The traction force devices are readily adjustable with respect to changing the force levels established by the devices. Such devices may also include means to limit the extent to which the corrective tractive apparatus can be extended or retracted during wearing of the appliance or accidently to protect the patient from injury, either during placement and removal of the appliance by the patient at the commencement and termination of treatment periods or because of misuse.

It is an object of the invention to provide an extraoral orthodontic appliance, including inexpensive traction force devices, for correcting dental-facial abnormalities, which can be worn intermittently by patients, and when worn, will apply a substantially constant tractive force level to the corrective tractive apparatus (face bow, set of J-hooks, chin cup, or the like) regardless of movement of the patient's head in any direction or of movements of the dental-facial structure.

It is a further object of the invention to provide an orthodontic appliance which will exert a substantially constant force level over the term of the treatment program phase requiring such force level and which can be readily adjusted by the treating orthodontist to other higher or lower force levels for use during other phases of the treatment program or for other patients.

A still further object of the invention is to provide an orthodontic appliance, including traction force devices which are force-biased by inexpensive non-constant (cumulative) force, clock-type springs, for correcting dental-facial abnormalities, which can be worn intermittently by patients, and when worn, will apply a substantially constant tractive force level to the corrective tractive apparatus regardless of movement of the patient's head or of movements of the dental-facial structure, and which is provided with means (associated with the traction force devices) to protect the patient from injury by the appliance during its placement or removal or because of its misuse.

Another object of the invention is to provide traction force devices for orthodontic appliances which have exceptionally long life and which can be used from patient to patient in association with various types of corrective tractive apparatus.

DESCRIPTION OF THE PREFERRED EMBODIMENTS

Figure 1:
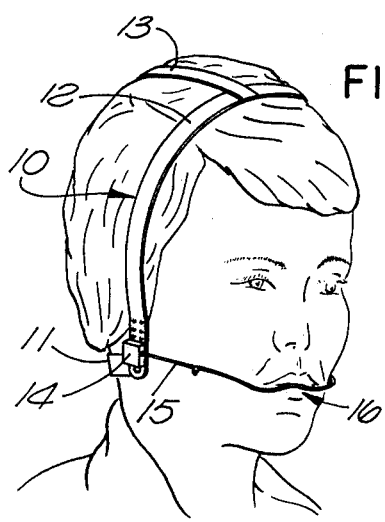
FIG. 1 is a perspective view of a patient wearing the extraoral orthodontic appliance, including a multi-band harness, according to the invention.

Referring to FIG. 1, an orthodontic appliance in accordance with the invention is shown in place on a patient's head. The appliance comprises: an orthodontic headgear or harness 10 in the form of a neckband 11 and connected headbands 12 and 13, providing cervical and occipital anchorage of the appliance on the patient's head; two traction force devices or force modules 14 (affixed to the harness 10 on each side thereof), each provided with a force transmission line or cable 15; and extraoral corrective tractive apparatus 16 connected to the cables 15 of the force modules 14. The force modules 14 apply a preset, substantially constant biasing force to the cables 15 in a direction toward such modules and the cables in turn apply such force to the tractive apparatus 16.

Figure 2:
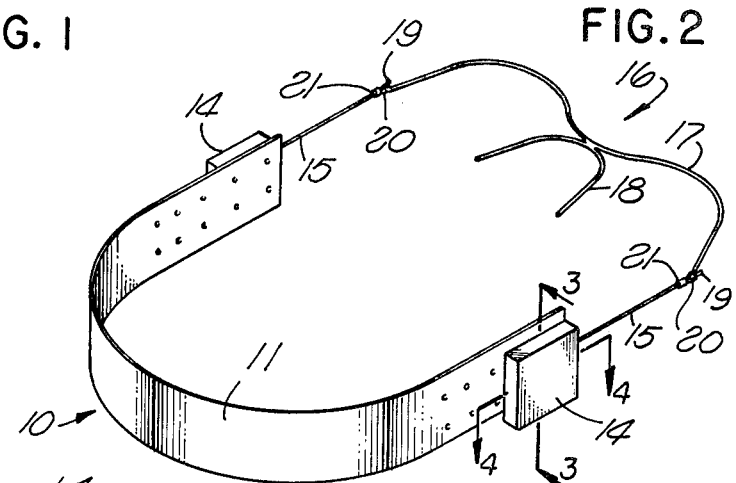
FIG. 2 is a perspective view of the appliance per se, including a cervical neckband, according to the invention.

The orthodontic appliance of the invention is further illustrated in FIG. 2 wherein the headgear or harness 10 is comprised of only a neckband 11 as the support for force modules 14 and the extraoral corrective apparatus 16 comprises a conventional face bow including outer bow member 17 and inner arch 18. The inner arch 18 of the face bow 16 may be non-angulated or angulated with respect to the plane of the outer bow 17 and the outer bow is provided with bow hooks 19 (or other connector means) for removable attachment to cables 15 via their end loops 20. The force lines or cables 15 may also include discs or other stop means 21 which protect the cables from complete withdrawal into their respective force modules when the appliance is not in use or when the cables are or become detached from tractive apparatus 16. It is also preferable that the force lines or cables 15 be made of a material displaying a specific tension strength or test strength (5-10 pound test) whereby they will break upon the application of excessive force (accidentally or through misuse) to the attached tractive apparatus 16 thereby to avoid injury to the wearer of the orthodontic appliance. In addition to face bows, the tractive apparatus 16 may comprise of conventional chin cups or J-hooks.

Figure 9:
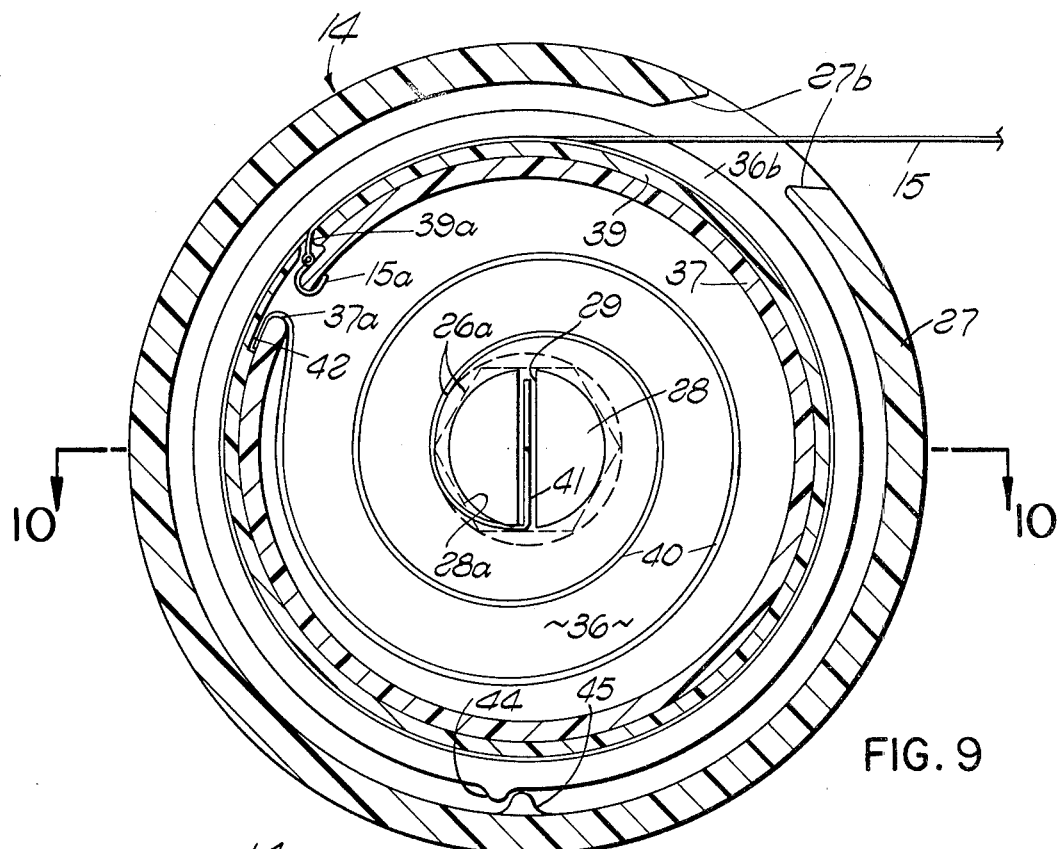
FIG. 9 is an enlarged sectional view of a still further alternative form of the traction force device of FIG. 3 wherein the force device is provided with means for adjusting the force level thereof after assembly of the device.
Figure 10:
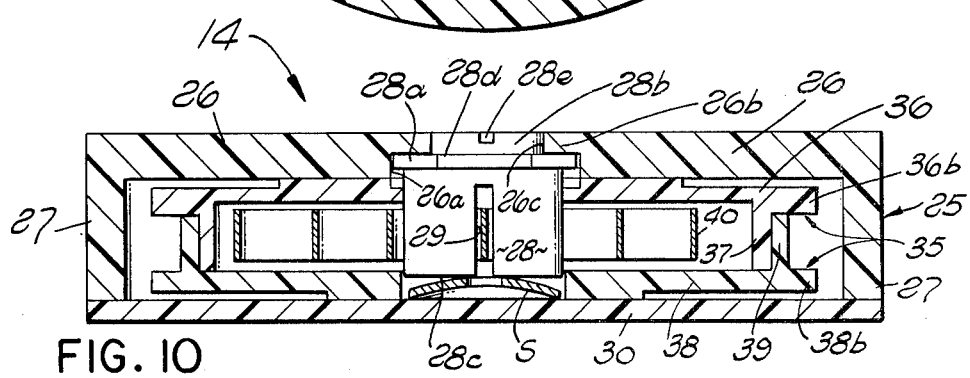
FIG. 10 is a transverse sectional view of the alternative form of traction force device of FIG. 9 taken along line 10—10 of FIG. 9.
Figure 11:
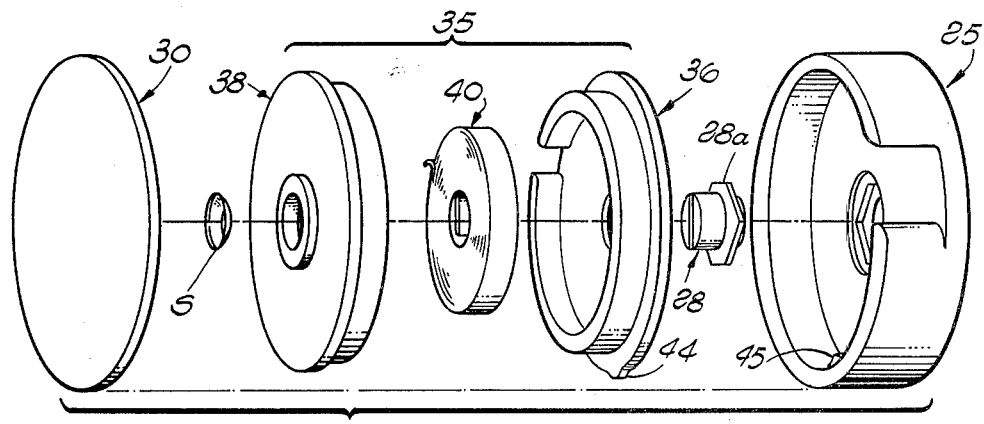
FIG. 11 is an exploded view in perspective of the alternative form of traction force device of FIGS. 9 and 10.

The headgear or harness 10, whether comprising a single neckband or a combination of a neckband and one or more headbands, is preferably adjustable to accommodate persons of different head size. The force modules 14, carried on each side of the harness, may be of any external configuration that is adaptable to manufacture and pleasing to the eye. The configuration of the force modules of FIGS. 1 thru 6 and FIG. 8 is rectangular, whereas the configuration of the force modules of FIGS. 9, 10 and 11 is round. Further, the external surface of such modules (particularly the cover surface) may be attractively decorated or inscribed with designs, initials, and the like. The force modules are preferably adjustably positionable along the neckband 11 in a rearward direction and along headband 12 in an upward direction, the latter positionability being required to effect an upwardly directed or "high pull" traction force to the extraoral corrective tractive apparatus 16. When the tractive apparatus 16 comprises a conventional face bow (FIG. 2) or a pair of J-hooks, such apparatus is removably attached to an appliance or orthodontic bracket fixed to the patient's teeth in such a manner that the appliance or bracket is worn continuously while the headgear 10 and tractive apparatus 16 are applied intermittently for a prescribed period of time each day, usually while the patient is sleeping.

Figure 3:
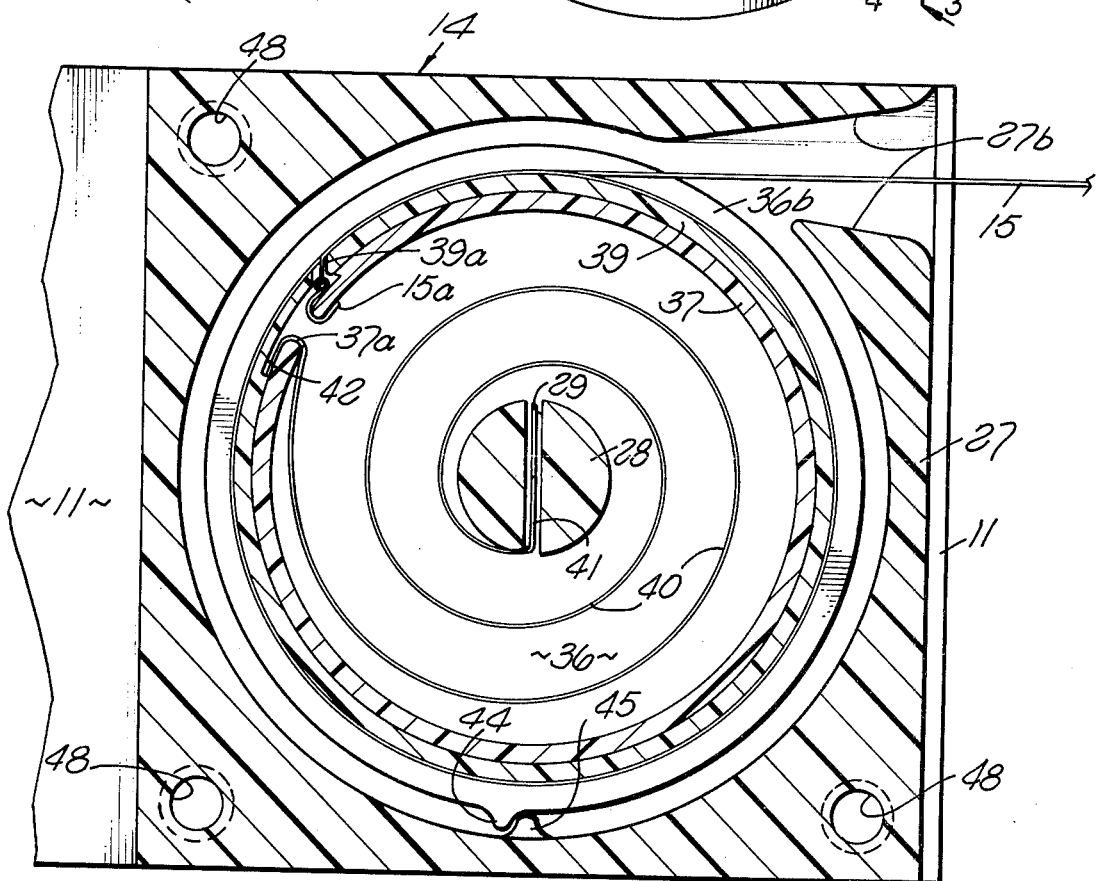
FIG. 3 is an enlarged sectional view of the traction force device on the line 3—3 of FIG. 2.
Figure 4:
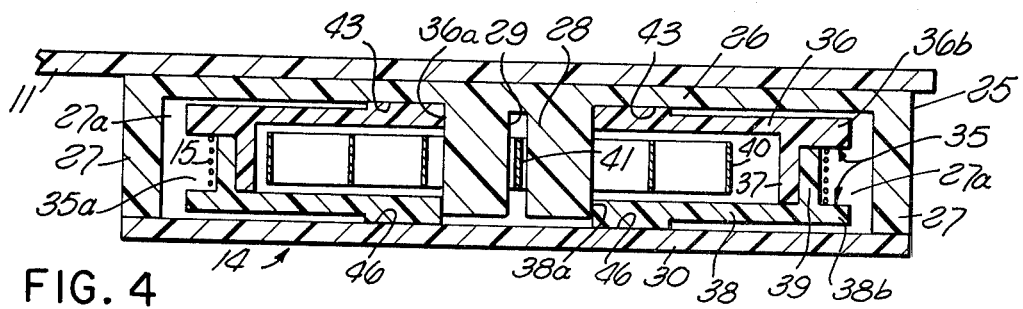
FIG. 4 is an enlarged sectional view of the traction force device on the line 4—4 of FIG. 2.

The force modules 14 (and their respective force transmission lines or cables 15) provide predetermined, substantially constant, force connection means between the harness 10 and the extraoral corrective tractive apparatus 16 on both sides of the appliance at all times regardless of relative movement between the head of the patient and the harness or of movements of the dental-facial structure. FIGS. 3 and 4 are sectional views of one preferred form of a traction force device 14 of the invention comprised principally of: a housing; an internally mounted, rotatable force reel and associated force biasing means; and a housing cover. The housing or case 25 is comprised of a base wall 26 adapted for adjustable mounting on harness 10 and side walls 27. The base wall 26 carries an integral central post or arbor 28 which has a transverse slot 29 extending to the base wall. The side walls 27 together with the central arbor define an annular space 27a within the housing 25 for receiving the force reel and biasing means. A removable housing cover 30 mates with the housing 25 to close the annular space 27a.

The force reel 35 is comprised of an inner spool 36, with an integral annular side wall 37, and an outer spool 38, with an integral annular side wall 39. The inner spool 36 is provided with a central circular opening 36a of a diameter such that the spool may be freely slipped onto the central post or arbor 28 of housing 25. The outer spool 38 is also provided with a central circular opening 38a of like diameter so that such spool may also be freely slipped onto arbor 28. The annular side wall 39 of the outer spool 38 has an inside diameter with respect to the outside diameter of the annular wall 37 of inner spool 36 such that these annular walls mate in overlapping fashion to form the reel 35. The spools 36 and 38 have annular rim portions 36b and 38b, respectively, which cooperate with the outer surface of annular wall 39 to form annular reel-trough 35a within which the force cable 15 is coiled as described hereinafter. The annular walls 37 and 39, respectively, of spools 36 and 38 mate in force fitment relationship so that the spools rotate together on arbor 28 as a unitary reel unit 35. Alternatively, the annular walls 37 and 39 may be appropriately keyed so that the spools 36 and 38 may be easily joined to form reel 35 or separated, yet when joined and positioned on arbor 28 within housing 25 from the desired unitary reel unit 35.

The force biasing means associated with the rotatable reel 35 of the module 14, in accordance with the invention, comprises a clock-type, flat spring 40 which develops non-constant (cumulative) forces during winding or unwinding. The inner end of the spring 40 has a folded portion 41 and the outer end of the spring has a hook-like portion 42. Spring 40 is positioned inside the inner spool 37 of the force reel and the desired biasing force is established as described hereinafter.

Assembly of force module 14 and establishment of the desired preset biasing force within the rotatable force reel 35 is accomplished by first placing the clock-type (cumulative force) coil spring 40 within the inner spool 36 with the outer hook-like portion 42 of the spring in hooked position in slot 37a located in the annular side wall 37 of such spool. The force transmission line or cable 15, for connecting the force module 14 with the extraoral corrective tractive apparatus 16, is next attached to the inner spool 36 via cable hook 15a placed in hooked position in slot 37a of side wall 37 of such spool. The outer spool 38 is thereafter appropriately mated with the inner spool 36, the annular side wall of the outer spool surrounding the side wall of the inner spool and together forming the force reel 35. A slot 39a in the side wall 39 of the outer spool permits passage of the cable 15 to the reel trough 35a formed by the mated spools.

Appropriate mating of spools 36 and 38 results in locked-in attachment of the outer end of coil spring 40 to the inner periphery of force reel 35 and of the cable 15 (via hook 15a) to the outer periphery of the reel, as shown in FIG. 3. Spools 36 and 38 are maintained together to form the unitary rotatable force reel 35 by force fitment between their respective side walls or by mating groove and key means formed in and on such side walls. The assembled reel (with internally contained coil spring) is next inserted into housing 25 with the center circular opening or aperature 36a of the inner spool first sliding over the central arbor 28 of the housing. As the reel 35 is progressively seated in the housing the inner end fold 41 of the spring is guided into the transverse slot 29 of arbor 28. Thus, the inner end of spring 40 becomes restrained or attached to the central arbor of the housing while the outer end of the spring remains attached (via hook-like portion 42) to the inner periphery of the inner spool. The force reel 35, when fully inserted into the housing 25, seats against the base wall 26 of the housing throughout an annular bearing surface 43 carried by inner spool 36 and surrounding the central opening 36a of such spool.

The inner spool 36 of force reel is provided, at one point on its rim 36b, with a projection 44. A similar and mating projection or reel stop 45 is provided within housing 25 on the base wall 26 at one point along the side wall 27. When the reel 35 is completely seated within housing 25 the spool projection 44 and reel stop 45 cooperate to limit the rotational movement of the reel to substantially one full turn. Thus, with force reel 35 seated, winding or unwinding movement of the spring is likewise limited to substantially one full turn. The biasing force developed by the spring (attached to the fixed central arbor and the inner periphery of the reel) during the permitted single turn ranges between the force exerted by the spring in its maximum unwound position (projection 44 in the position shown in FIG. 3 with respect to stop 45) and a higher force level established when the spring is wound over the distance of substantially one turn to the point where the reel 35 is again inhibited from further rotational movement by projection 44 and stop 45.

With the force reel 35 in fully seated position within housing 25, the cable 15 is wound around the reel until a predetermined number of cable loops are formed within reel trough 15a. The cable is thereafter led out of the housing through opening or passageway 27b. The housing 25 of the force module 14 is closed, with the force reel retained in proper alignment therein, by seating cover plate 30 to side wall 27 of the housing. With the cover plate properly seated an annular bearing interface is established between the cover and the force reel. Such interface occurs between the annular bearing surface 46 carried by the outer spool 38 and surrounding the central opening 38a of such spool and the inner surface of the cover plate 30.

Figure 5:
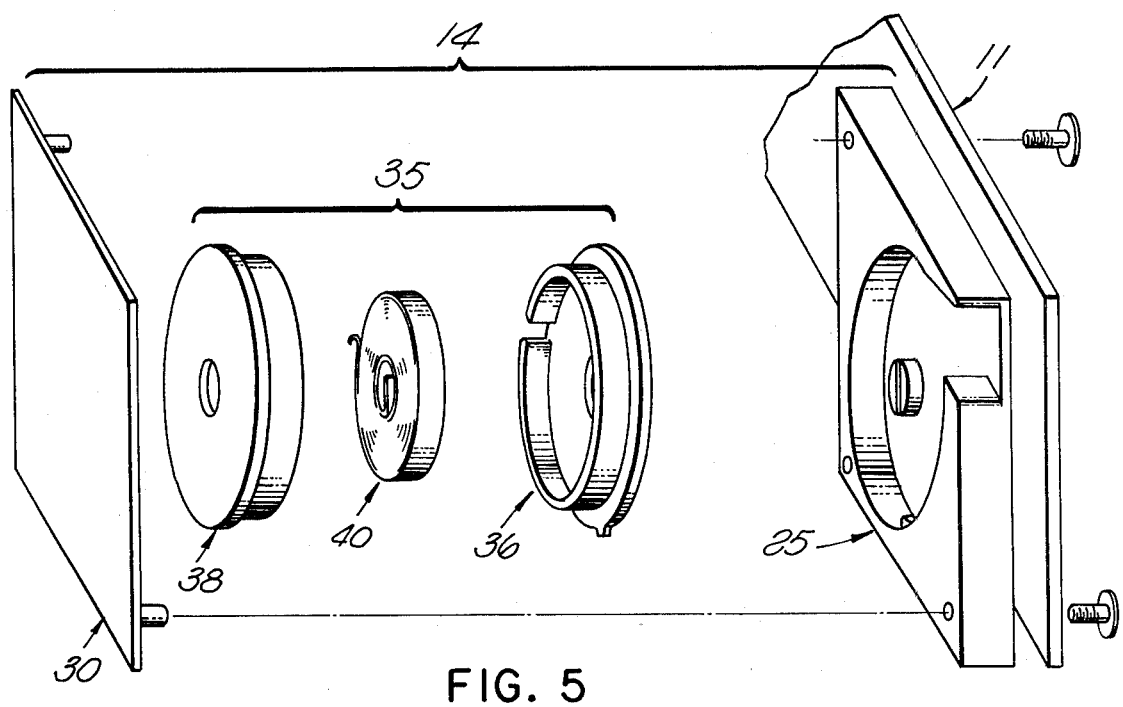
FIG. 5 is an exploded view in perspective of the traction force device of FIGS. 3 and 4.

The cover plate is maintained in its seated position by appropriate fastener means (not shown in FIG. 3 and FIG. 4) which extend through the cover plate and through holes 48 in the housing 25. Such fastener means may also be utilized, by extension through appropriate matching holes in the bands forming the extraoral harness, to hold the force module 14 (comprised of the housing 25, cover plate 30, and force reel 35) in a predetermined position on the harness. FIG. 5 shows the items comprising the traction force device or force module 14 (as illustrated in detail in FIG. 3 and FIG. 4 and described heretofore) in an exploded view in perspective.

The common range of tractive pull forces applied during orthodontic treatment programs is 4 to 32 ounces on each side of the face bow or other extraoral tractive apparatus of typical headgear assemblies. The readily available clock-type (cumulative force) springs of the type used in the force module of this invention are typically about twenty-four inches long (in their fully extended state) and have a width of about one-eighth inch and a material thickness of about 0.010 inch. When coiled inside of a seven-eighths inch diameter spool and around a one-quarter inch arbor, a maximum force with the springs completely wound (all coils tightly in contact with adjacent coils) of about 32 ounces may be developed. Other available clock-type coil springs, for use as the biasing force means within force module 14 of the invention, may develop tension forces in the range of one-half to 3 pounds depending on their dimensions. All like springs provide continuous intermediate ranges of pull force between their unwound and wound state, i.e., 0–32 ounces.

Non-constant or cumulative force coil springs having force ranges and a dimensional configuration as described above are commonly made of strips of flexible high-carbon spring steel or stainless steel having a thickness on the order of 0.003–0.015 inches, with the original uncoiled strips having lengths of 20 to 70 or more inches. In their coiled but unwound state (no traction force) they may contain as few as 5 coils and as many as 15 coils or more with the number of coils increasing in number when such springs are fully wound. Such springs provide essentially a continuously increasing force with extension. Therefore, since the normal range of head or jaw movement results in only 1–2 inches of extension, the force variation experienced due to this extension is only a small portion of the total force range of the springs as will be more fully explained hereinafter with respect to FIG. 7. Thus, the springs used in the traction force device or force module, in accordance with the invention, result in the application of a relatively constant, adjustably predetermined, corrective force during an orthodontic treatment program even during periods of substantial head or jaw movement.

To adjust or preset the traction force level to be applied by a force module 14 of the orthodontic appliance of the invention, a non-constant force coil spring (having a force range encompassing the desired force level) is selected and installed in the force reel 35 as previously described and shown in detail in FIG. 3 and FIG. 4. During seating of the reel in housing 25 (with the inner end 41 of the coil spring 40 within transverse slot 29 of housing arbor 28, but before the reel reaches its fully seated position adjacent base wall 26 of the housing) the spring 40 is wound by rotation of the force reel in the direction which will wind it further around the arbor, thus increasing the biasing force of the spring. Winding of the spring is continued until the tangential force at the perimeter of the reel (force cable coiling surface in reel trough 15a) is substantially equal to the desired traction force level. An additional one-half winding turn is applied to the reel and seating of the reel within housing 25 is completed. With the reel 35 in its fully seated position and the winding force removed therefrom, the reel automatically rotates (under force of the spring) to the position shown in FIG. 3 whereat the projection 44 on the rim 36b of inner spool 36 mates with reel stop 45 to restrain the force reel 35 from further rotation (and unwinding of spring 40).

Winding of the force reel 35, to establish a desired preset force level for a force module 14, may be accomplished by pulling on the force cable 15 connected to the reel and coiled thereabout in reel trough 15a. During such spring-reel winding procedure the pull force on the cable is increased and measured (or continued until a predetermined extension is reached) until the desired force level is reached. As the force reel is wound to obtain the force level to be preset for the force module, the force cable uncoils from the reel. After the wound reel is fully seated in the housing 25 and has rotated in its spring biasing direction to its stop position (projection 44 and stop 45 mated), the force cable 15 may be again coiled on the reel until only an appropriate length thereof remains uncoiled for extension from the force module and coupling to the extraoral tractive apparatus 16. Alternatively, an appropriate length of the force cable may be cut off and the end leading from the force module attached to a fitting for coupling to the extraoral tractive apparatus. At the preset force level the mating projection 44 and reel stop 45 permit the force cable to be extended only during one revolution of the reel and thus over a linear distance equivalent to the circumferential distance a point on the reel trough travels during such revolution, a distance of about 2 to 4 inches depending upon the diameter of the reel (about 0.6 to 1.3 inches).

Figure 6:
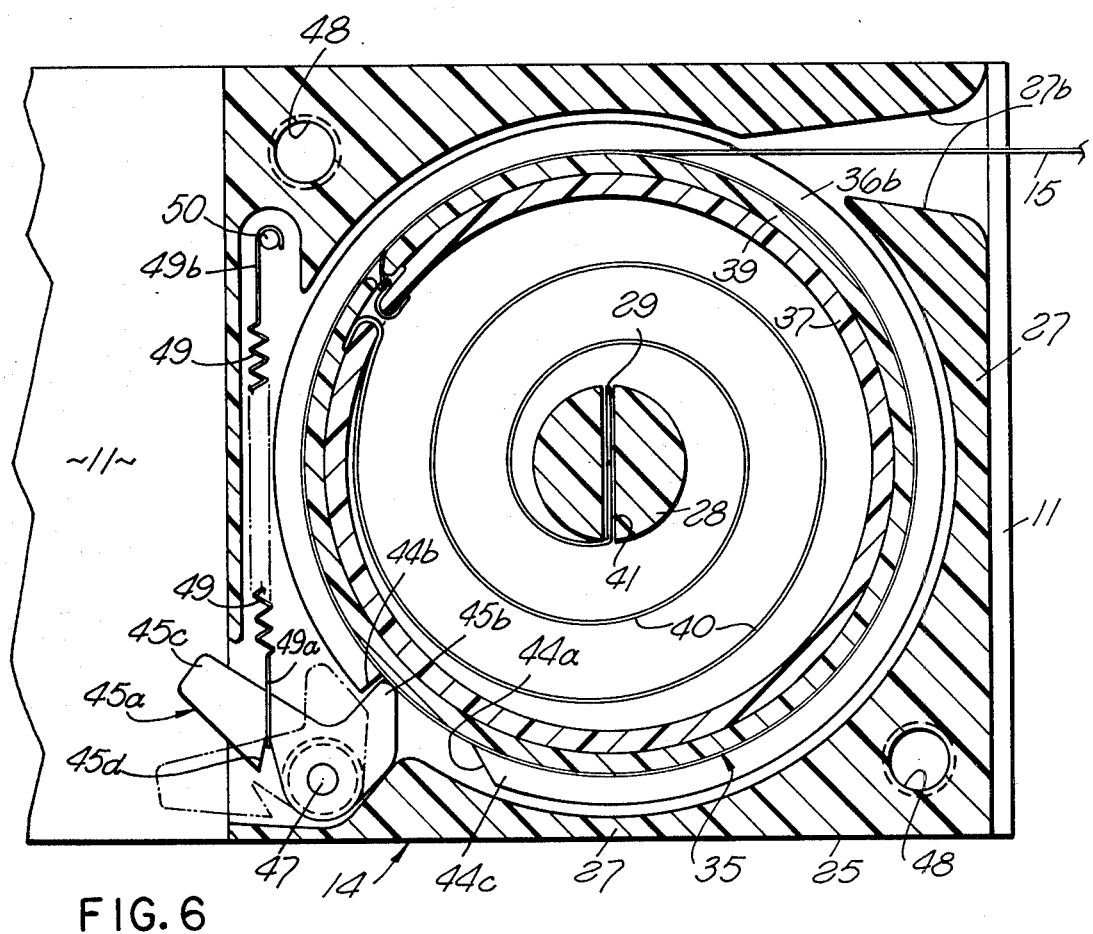
FIG. 6 is an enlarged sectional view of an alternative form of the traction force device of FIG. 3.

In FIG. 6 an enlarged sectional view is presented of another preferred form of a force module or traction force device 14 in accordance with the invention. As shown, the force module components are essentially of a design and function as described with respect to the force module of FIGS. 3 and 4. The annular rim portion 36b of inner spool 36 of the force reel is not, however, provided with a projection 44 and housing 25 is not provided with a mating projection or reel stop 45 as shown in FIG. 3. Rather, the rim portion 36b of spool 36 contains an open segment 44a with an abutment portion 44b constituting the mechanical equivalent of the projection 44 of the embodiment of the invention shown in FIG. 3. In lieu of the reel stop 45 of the FIG. 3 embodiment, a reel stop mechanism 45a is provided within the housing 25, at one corner thereof, such mechanism being pivotally mounted on a post 47 and having a reel stop portion 45b and stop release portion 45c.

The reel stop mechanism 45a is normally force biased (by a spring 49 which is hooked at its end 49a into slot 45d of the stop mechanism and at its end 49b to post 50 carried by the housing 25) so that reel stop portion 45b is within notched segment 44a of rim 36b in abutment with portion 44b of the rim. The abutment portion 45b of the reel stop mechanism is precluded from releasing the spool rim 36b (and thus reel 35) for rotation in the direction of the spring unwinding force applied to reel 35 by spring 40 because of shoulder 27c of side wall 27. The force reel 35 may be freed for rotation in such direction by applying finger pressure to the release portion 45c of the stop mechanism 45a so as to pivot same about post 47 to the reel release position (shown in phantom), said finger pressure being applied to the extent necessary to overcome the force of spring 49 and rotational force applied to stop portion 45b by abutment 44b. With the stop mechanism in its release position the force reel is free to rotate in the direction of the spring unwinding force so-long-as: such force is present; no contra-rotational force is applied to the reel by cable 15; and the mechanism is not released to again perform its reel-stop function.

The force reel 35 (and internal spring 40) of the force module 14 shown in FIG. 6 may be wound by rotating the reel (by hand or by pulling cable 15) against the unwinding force of the spring. During such winding the stop mechanism 45a may be held in its release position or is forced to such position by spool rim 36b after first being deflected to its release position by the inclined configuration of abutment 44c of such rim. As in the case of the force module shown in FIGS. 3 and 4, the invention contemplates that after the force reel has been preset (by winding) to a desired force level and the extraoral headgear adjusted to the patient's dental-facial size and structure and the intraoral orthodontic fixtures through which the treatment forces are to be applied, only about one revolution of the force reel will occur during normal head and jaw movements. The force module embodiment of FIGS. 3 and 4, in fact, only permits one rotation of the reel because of abutment 44 on the spool rim 36b and reel stop 45. The force module embodiment of the invention as shown in FIG. 6, however, provides an additional safety feature whereby, if during placement or removal of the appliance (or its misuse) the corrective tractive apparatus (face bow, chin cup, etc.) and connected force transmission lines or cables are extended, and accidently released; injury to the patient will be precluded because the reel stop mechanism 45a automatically stops rotation of the force reels after one revolution. It is also apparent that the force module embodiment illustrated in FIG. 6 results in ease in the donning and doffing of the associated corrective tractive apparatus.

Figure 7:
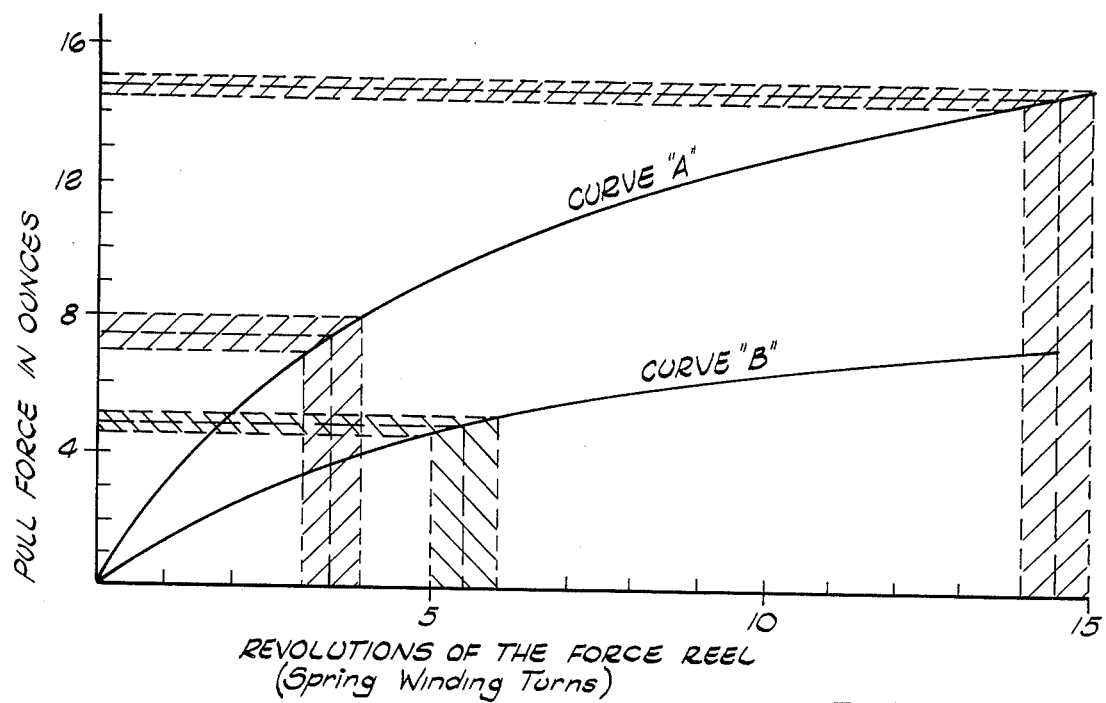
FIG. 7 is a graphic presentation of force extension curves for typical non-constant force, clock-type springs within traction force devices according to the invention, illustrating the substantially constant corrective tractive force levels attainable for representative adjustments to the traction force devices.

The effect of utilizing relatively inexpensive non-constant (cumulative) force, clock-type, springs in force modules (in accordance with the invention) to achieve application of substantially constant predetermined forces to corrective orthodontic tractive apparatus, is more fully illustrated in FIG. 7 by the force extension curves for two of such springs. Curve "A" presents the force characteristics of a spring useful for developing forces of up to 16 ounces. Fifteen revolutions of the force reel are required to completely wind the spring. If the orthodontic treatment program requires that the force modules of the appliance apply a corrective traction force of 30 ounces of total force, the force reel of each module is wound to between 14 and 15 revolutions and fully seated in the housing of the force module. The reel of each module, if of the embodiment shown in FIGS. 3 and 4, is thus permitted (by projection 44 and stop 45) to rotate during the treatment program between the 14th and 15th revolution positions and provides a tractive force range, via its force cable, of between 14.5 and 15.0 ounces, the force of both modules adding to a total of 29–30 ounces. With the orthodontic appliance (harness, pair of force modules and force cables, and corrective tractive apparatus) adjusted in its normal patient placement, the force cables position each force reel approximately midway through their single allowable revolution and at an individual traction force level of 14.75 ounces (total force level for the pair of modules of 29.5 ounces). Movement of the patients head and/or dental-facial structure will result in positive or negative changes in applied force of only ±0.5 ounces. Thus, the maximum deviation in applied force from the desired treatment force level is 1 ounce or ±1.7%. This percentage of deviation is at least as favorable as force deviations for constant force springs or other known means and devices for developing corrective tractive forces in orthodontic treatment programs. If the corrective program requires only 15 ounces of total force delivered via the orthodontic appliance, each force module must provide 7.5 ounces of force which is attained by prewinding such modules to $3\frac{1}{2}$ revolutions. The variation in force from 7.5 ounces is ±0.5 ounces for each module or ±6.7%. This range for variation of force (due to head and/or jaw movement) is still essentially constant when compared to the force variation in other headgears used in orthodontic treatment programs.

Curve "B", illustrated in FIG. 7, presents the force characteristics of a spring capable of developing forces of up to $7\frac{1}{2}$ ounces over 15 winding revolutions of the force reel containing same. If a treatment traction force (applied by the two force reels and force cables) of 10 ounces is required, the force reel of each force module is wound to between 5 and 6 revolutions and then fully seated in the force module housing. As shown in FIG. 7, the force reel is permitted to rotate (one revolution) over force range of 4.7 ounces of 5.2 ounces. The resultant mid-rotation force level for each force module is 4.95 ounces and the total applied force is 9.9 ounces ±0.5 ounces. Movement of the patients head and/or dental-facial structure will result in positive or negative changes in the applied force of only ±0.5 ounces. Thus, the maximum deviation in total applied force from the desired treatment force level of 10 ounces is 6%.

Figure 8A:
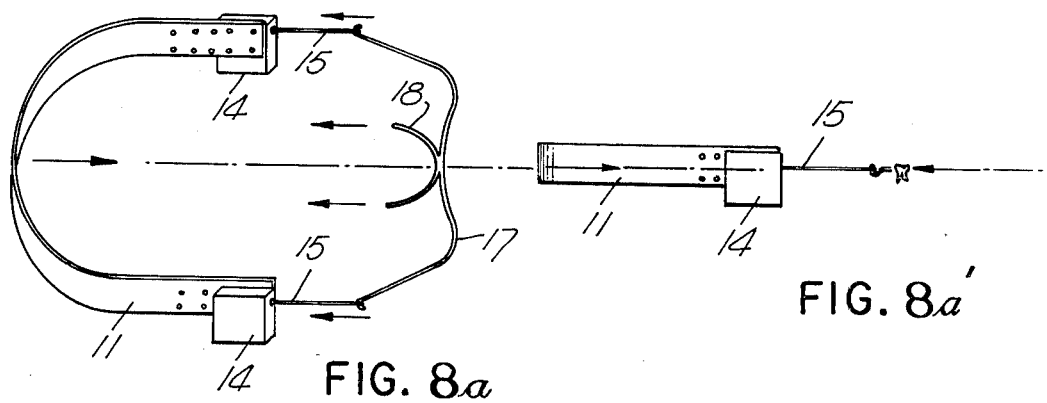
FIGS. 8a, 8a', 8b, and 8b' comprise a series of force diagrams illustrative of how tractive forces, generated by the traction force devices of the invention are applied through connected conventional corrective apparatus to the dental-facial structure.
Figure 8B:
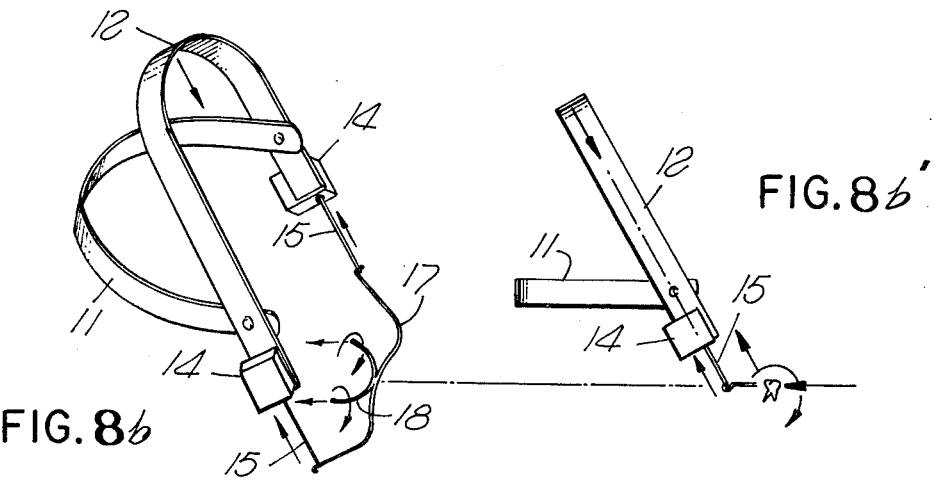

To further illustrate the manner in which the invention utilizes the extraoral pull forces developed by force modules 14 to apply intraoral corrective forces to teeth, representative force diagrams (perspective and schematic) are presented in FIG. 8. FIG. 8a is a perspective view of the appliance, including only a cervical neckband 11 to support the force modules, with alignment such that the band, force modules, force cables and a face bow translate straight pull forces (developed via force modules 14) into straight parallel intraoral tractive forces applied to the teeth to be moved, as shown in force diagram 8a. FIG. 8b is a perspective view of a multi-band harness to provide a "high-pull" during orthodontic treatment. The elevated position of the force modules carried on band 13, with the face bow 17 and inner arch 18 maintained in a substantially horizontal plane (as shown in force diagram 8b) by the tooth brackets (now shown), results in the intraoral application of "high-pull" forces together with rotational forces on the teeth to be repositioned.

In FIG. 9 there is presented an enlarged sectional view of still another form of a force module or traction force device 14 in accordance with the invention. As shown, the force module components are essentially of a design and function as described with respect to the force module of FIGS. 3 and 4. From a nonfunctional appearance viewpoint the housing 25 and housing cover 30 have been shown to have a round or circular configuration. From a functional viewpoint the central post or arbor 28 is not shown as an integral part of the base wall 26 of housing 25. Rather, the arbor 28 is separable from the base wall as a force-adjusting unit including an arbor-locking hexagonal (or octagonal) head portion 28a and an annular arbor-adjusting portion 28b. As more fully shown in FIG. 10, the force-adjusting arbor unit is normally maintained in the base wall 26 with its head portion 28a positioned within a cavity 26a and seated against base wall portion 26b. The cavity 26a presents two annular configurations to the outer periphery of the arbor head portion 28a. In the fully seated position shown, the cavity 26a presents a mating hexagonal (or octagonal) configuration to the arbor head whereby the head is precluded from turning and the arbor 28 functions in the manner as the fixed arbor of the force device of FIGS. 3 and 4. In this position the annular arbor-adjusting portion 28b of the force-adjusting unit extends through a matching round opening 26c in base wall 26. The force-adjusting arbor unit is maintained in its fully-seated position by spring means S of any suitable type located between housing cover 30 and end face 28c of arbor 28. When the arbor unit is unseated (as described hereinafter) the cavity 26a presents a round configuration within which such unit may be rotated.

The exposed end face 28d of arbor-adjusting portion 28b of the force-adjusting arbor unit presents a slot 28e for receiving a screwdriver head. To adjust the force level of the force device 14 (wind or unwind spring 40) the arbor unit is pushed toward the cover 30 of the force device by a screwdriver head positioned within slot 28e using sufficient pushing force to overcome the contra-force of spring S. As the arbor unit moves toward the cover 30 the arbor head portion 28a leaves the portion of cavity 26a in base wall 26 presenting a mating (arbor locking) configuration (hexagonal, octagonal, etc.) and becomes positioned in the portion of cavity 26a presenting a round configuration whereby the arbor unit may be turned in either direction by the screwdriver to wind or unwind spring 40. During the winding or unwinding procedure force reel 35 (comprised of inner spool 36 and outer spool 38) is precluded from rotating more than one turn by spool projection 44 and reel stop 45 as described in connection with the force device embodiment shown in FIGS. 3 and 4. After winding or unwinding spring 40 through rotation of the force-adjusting arbor unit the pushing force applied to the unit via the screwdriver head is released so that the arbor head portion 28a reseats in the locking portion of cavity 26a whereby the new force level established by spring 40 within module 14 is maintained.

The cover plate 30, for the force module or traction force device 14, as shown in FIGS. 9 and 10, is positioned and maintained by appropriate fastener means (not shown). Such fastener means may also be utilized to hold the force module in a predetermined position on a headgear or head harness. FIG. 11 shows the items comprising the embodiment of the traction force device 14 illustrated in FIGS. 9 and 10 in an exploded view in perspective.

There has been described several forms of an orthodontic appliance in which relatively inexpensive force modules (incorporating non-constant, cumulative force, clock-type, coil springs) provide a full and adjustable range of corrective traction forces for moving malpositioned teeth, the corrective traction force of such modules remaining relatively constant at the preset force level even during periods of substantial head or jaw movement. As used in the force modules of the invention, the springs (in their force reel biasing location) are limited in their winding and unwinding movement so as to assure application of the relatively constant, preset force level to the corrective tractive apparatus during the periods of orthodontic treatment and to protect the patient from injury during placement and removal of the appliance.

Through the invention the orthodontists control of the treatment program is substantially improved and the desired force level for tooth movement or other orthodontic correction is easily achieved by winding adjustment of the force reel and/or the central arbor unit within each force module. The selected force level then remains essentially constant during head and/or jaw movement and the desired treatment period.

What is claimed is:

1. In an orthodontic appliance having a harness for mounting on the head and/or neck of a patient and a corrective tractive apparatus to apply substantially equal extraoral traction forces in orthodontic treatment to selected like-portions of both sides of the dental-facial frame of the patient, the improvement comprising:

traction force means mounted on said harness on each side thereof and including a housing, a force reel rotatably mounted within said housing, and a cumulative-force clock-type spring located within said reel, said spring being fixedly mounted at its inner end to said housing and at its outer end to said reel and being windable with said reel to provide a range of biasing force levels to the reel in one rotatable direction;

cables on each side of said harness having one end extending into a respective housing of a traction force means and being attached to the reel mounted therein and coiled in multiple windings thereabout in a direction opposed to the spring-biased rotatable direction thereof, the biasing force of the reel tending to further wind said cable about said reel, and the free end of said cable being adapted for attachment to the corrective tractive apparatus on its respective side of said harness to apply the biasing force of the reel as a traction force to said apparatus; and means associated with each traction force means for limiting the rotational movement of the force reel in its spring-biased rotatable direction after said reel has been wound to the desired force level whereby during the period of orthodontic treatment utilizing the appliance the biasing force provided by each cumulative-force spring, as it winds or unwinds in response to movement of the dental-facial frame, results in the application of a limited range of corrective tractive forces that closely encompass the desired force level.

2. The orthodontic appliance as defined in claim 1 wherein the means associated with each traction force means for limiting the rotational movement of each force reel restricts the rotation thereof in its spring-biased rotatable direction to approximately one revolution.

3. The orthodontic appliance as defined in claim 1 wherein the means associated with each traction force means for limiting the rotational movement of each force reel comprises a pair of mating stops, one of said stops consisting of a projecting portion of the reel at its outer periphery and the other of said stops consisting of a projecting portion of said housing in the rotational path of the projecting portion of the reel whereby the reel is rotatable only over a distance of substantially one turn.

4. The orthodontic appliance as defined in claim 1 wherein the means associated with each traction force means for limiting the rotational movement of each force reel comprises a reel stop mechanism pivotally mounted within said housing at a point adjacent to the periphery of said reel and a single limited open segment of the reel at its periphery, said open segment presenting a radially extending abutment surface for interference with said stop mechanism when in its reel stop position to limit rotation of the reel to substantially one turn in the direction of the biasing force created by the spring within said reel.

5. The orthodontic appliance as defined in claim 4 wherein the open segment of the reel presents an outwardly inclined abutment surface opposing the radially extending abutment surface of said open segment whereby during reel rotation in the direction opposite to the biasing force created by the spring within said reel the pivotally mounted reel stop mechanism is deflected out of its reel stop position by said inclined surface to permit continuing rotation of said reel in said opposite direction.

6. The orthodontic appliance as defined in claims 4 or 5 wherein the reel stop mechanism is normally spring biased into its reel stop position and said mechanism is provided with a stop release portion extending to a point beyond said housing whereby said mechanism may be released from its reel stop position by application of a force to said release portion, from a point external to said housing, overcoming the biasing force normally applied to said mechanism.

7. The orthodontic appliance as defined in claim 1 wherein the cables extending from and connecting the traction force means to the corrective tractive apparatus are made of a material displaying a specific tensile strength whereby they will break upon the application of excessive force (accidentally or through misuse) to said tractive apparatus thereby to avoid injury to the patient.

8. In an orthodontic appliance having a harness for mounting on the head and/or neck of a patient and a corrective tractive apparatus to apply substantially equal extraoral traction forces in orthodontic treatment to selected like-portions of both sides of the dental-facial frame of the patient, the improvement comprising:

traction force means mounted on said harness on each side thereof and including a housing having a central arbor projecting from one wall thereof, said arbor being axially positionable with respect to said housing wall, a force reel rotatably mounted on said arbor within said housing, and a cumulative-force clock-type spring located within said reel, said spring being fixedly mounted at its inner end to said arbor and at its outer end to said reel and being windable with said reel to provide a range of biasing force levels to the reel in one rotatable direction;

cables on each side of said harness having one end extending into a respective housing of a traction force means and being attached to the reel mounted therein and coiled in multiple windings thereabout in a direction opposed to the spring-biased rotatable direction thereof, the biasing force of the reel tending to further wind said cable about said reel, and the free end of said cable being adapted for attachment to the corrective tractive apparatus on its respective side of said harness to apply the biasing force of the reel as a traction force to said apparatus; and means associated with each traction force means for limiting the rotational movement of the force reel in its spring-biased rotatable direction after said reel has been wound to the desired force level whereby during the period of orthodontic treatment utilizing the appliance the biasing force provided by each cumulative-force spring, as it winds or unwinds in response to movement of the dental-facial frame, results in the application of a limited range of corrective tractive forces that closely encompass the desired force level.

9. The orthodontic appliance as defined in claim 8 wherein the axially positionable central arbor projecting from one wall of the housing includes an arbor-locking head portion whereby when the arbor is in a fully-seated position on said side wall the head portion of said arbor engages a lock portion of said housing wall thereby locking the arbor against rotation within said housing and when the arbor is axially moved out of its fully-seated position said head portion disengages from said lock portion of said housing wall thereby permitting rotation of the arbor and winding or unwinding of the cumulative-force clock-type spring within said housing.

10. The orthodontic appliance as defined in claim 9 wherein means are provided to normally force-bias the axially positionable central arbor of the housing into the fully-seated position on the housing wall.

11. The orthodontic appliance as defined in claim 10 wherein the axially positionable central arbor of the housing includes an arbor-adjusting portion accessible through an opening in the housing wall, said arbor-adjusting portion presenting means by which said arbor may be axially moved against the force-biasing means to disengage the arbor-locking head portion from the lock portion of said housing wall and rotated to adjust the force level established between the cumulative-force clock-type spring fixedly mounted to said arbor and said force reel.

* * * * *